United States Patent [19]

Dilday

[11] 4,379,144

[45] Apr. 5, 1983

[54] PROCESS FOR PRODUCING A FLOWABLE FUNGICIDE FORMULATION

[75] Inventor: Joseph T. Dilday, North Little Rock, Ark.

[73] Assignee: Olin Corporation, New Haven, Conn.

[21] Appl. No.: 252,667

[22] Filed: Apr. 9, 1981

Related U.S. Application Data

[63] Continuation of Ser. No. 71,227, Aug. 30, 1979, abandoned.

[51] Int. Cl.³ .............. A01N 61/02; A01N 33/18; A01N 43/78; A01N 43/80
[52] U.S. Cl. .............. 424/168; 424/263; 424/270; 424/273 R; 424/274; 424/326; 424/349
[58] Field of Search .............. 424/168, 273 R, 349, 424/274, 326, 263, 270

[56] References Cited

U.S. PATENT DOCUMENTS

| | | | |
|---|---|---|---|
| 3,157,486 | 11/1964 | Harrison et al. | 71/2.4 |
| 3,720,684 | 3/1973 | Krenzer et al. | 424/270 |
| 3,830,925 | 8/1974 | Rathgeb | 424/270 |
| 3,948,636 | 4/1976 | Marks | 424/304 |
| 4,107,318 | 8/1978 | Albrecht et al. | 424/273 R |

FOREIGN PATENT DOCUMENTS

| | | | |
|---|---|---|---|
| 46-6435 | 2/1971 | Japan | 424/168 |
| 46-6438 | 2/1971 | Japan | 424/168 |
| 46-18514 | 5/1971 | Japan | 424/168 |
| 970579 | 9/1964 | United Kingdom | |

OTHER PUBLICATIONS

NL Industries, Inc.–Data Sheets–Geopon TS–136, GA Series Gellont.
Olin Corp. Data Sheet for Terrazole & Terraclor.
Exxon Data Sheet DG–1P–Isopar M (1978).
ICI Americas Inc.–Data Sheet Atphos.
Degussa–Data Sheet–Aerosil.

*Primary Examiner*—Douglas W. Robinson
*Attorney, Agent, or Firm*—William A. Simons; Thomas P. O'Day

[57] ABSTRACT

Disclosed is a process for producing a flowable fungicide formulation comprising the steps of:
(a) heating sufficiently a mixture of at least one solid active fungicidal compound with a hydrocarbon solvent and surfactant to form a melt;
(b) adding sufficient aqueous solution to said melt to form a water-in-oil emulsion;
(c) thoroughly mixing said emulsion in the presence of sufficient thickening agent to form a stable flowable fungicide formulation.

28 Claims, No Drawings

PROCESS FOR PRODUCING A FLOWABLE FUNGICIDE FORMULATION

This is a continuation of application Ser. No. 071,227, filed Aug. 30, 1979 now abandoned.

BACKGROUND OF THE INVENTION

1. Field of the Invention

This invention relates to a process for producing a flowable fungicide formulation.

2. Description of the Prior Art

In the art of fungicide formulation, three types of commercial products are commonly available today. These types of products are as follows:

1. True liquid solutions—made by dissolving an active fungicidal compound in a suitable solvent (e.g., xylene);
2. Wettable powders—made by grinding an active fungicidal compound with a selected inert clay (e.g., silica-containing material) in air mill, roller mill, ball mill or the like to obtain a fine powder having a particle size of about 1 to about 5 microns;
3. Flowable formulations—made by grinding an active fungicidal compound with a clay to obtain a small particle size either before or after forming a suspension of solids in water by a thorough mixing step (e.g., in a high shear mixer).

Because of handling problems and lack of ease in application with solid materials like wettable powders, farmers have favored liquid application of fungicides to soil, seeds and agricultural vegetation. Moreover, because true liquid solutions generally can be made more cheaper than flowables, fungicide manufactures have generally favored the making of the former type of formulation.

However, for certain kinds of applications, true liquid solutions of fungicidal material are not preferred. For example, the employment of flowable formulations has been favored over true solutions for the fungicidal treatment of agricultural seeds. A principal reason for this favorism is that seeds which have been treated with a fungicide are normally required by governmental regulations to be dyed an unnatural color (e.g., bright red or violet) to disassociate treated seeds from untreated seeds. Accordingly, fungicide formulations employed in seed treatment also contain a minor amount of a dye. It has been found that flowables are better able to transfer that dye to the seeds than conventional true solutions.

Another obstacle which prevents the universal use of true solutions of fungicides has to do with the selection of a suitable solvent. Such solvents must possess several properties. They must be inert to the active fungicidal material so as to not inactive its fungicidal properties. Furthermore, the solvent must still be able to dissolve it; and yet be harmless to the crops and agricultural environment being treated. Xylene, because it generally possesses such suitable properties, has been the solvent of choice for many fungicial applications. But, there are problems associated with xylene. This solvent possesses an odor which is objectionable, causing complaints from handlers and farmers. Also, the solvent has a flash point of about 80° F., causing the products to carry a flammable label for transportation, which means higher freight rates and more restrictions on transportation, storage and use. Furthermore, distributors and farmers who employ xylene may have their insurance rates raised because of its "flammable" property. Further, because xylene is an aromatic petroleum product, its supply is increasingly smaller. Still further, when xylene-dissolved products are used in seed treatments, the presence of xylene appears to dull the brightness of the dyed color on the seeds, thus making it more difficult to disassociate treated seeds from untreated seeds.

With such problems surrounding true liquid solutions of fungicides, farmers are increasingly turning to the use of flowable formulations, especially in the treatment of seeds. However, in the past, the production of flowable formulations has been relatively time consuming and expensive, mainly because of the grinding step that is necessary to reduce the size of solid fungicidal compounds. This size reduction is necessary to allow the fungicide materials to remain in the suspension. But, such grinding steps require relatively expensive equipment and are carried out at a slow rate. Thus, until now, it has been normally uneconomical to make flowable fungicide formulations starting with solid, as opposed to liquid, active fungicidal compounds.

Therefore, there is a need in the art to find a new process for producing flowable fungicide that can economically utilize solid fungicidal compounds without grinding. The present invention is directed to a process that eliminates such unwanted grinding steps.

BRIEF SUMMARY OF THE INVENTION

Accordingly, the present invention is directed to a process for producing a flowable fungicide formulation comprising the steps:

(a) heating sufficiently a mixture of at least one solid active fungicidal compound, hydrocarbon solvent and surfactant so as to form a melt;

(b) adding sufficient aqueous solution to said melt to form a water-in-oil emulsion;

(c) thoroughly mixing said emulsion in the presence of sufficient thickening agent to form a stable flowable fungicide formulation.

DETAILED DESCRIPTION

Flowable fungicide formulations (sometimes referred to hereafter as "flowables") are generally known in the art as a suspension of solid materials such as clays and the like mixed with an active fungicidal material in water. Flowables have a creamy consistency which may or may not necessarily be added with more water just prior to application. Flowables may contain minor amounts of other ingredients such as surfactants, antifreezes such as propylene glycol, dyes to further improve the properties of the flowables. The active fungicidal ingredient or ingredients may originally be either liquid or solid in nature when formulated into the flowables. In the past, commercial flowables, to the best knowledge of applicant, did not contain any hydrocarbon solvents. And as stated above, prior art processes for making flowables required the use of a grinding step when solid fungicidal materials were used.

The present process for making flowables does not require this costly and slow grinding step. Specifically, the melting step (a), of the present process, mentioned above, effectively reduces the particle size of solid fungicides so that the solid fungicidal compounds will remain in the formulation and not readily precipitate out. Further, the employment of hydrocarbon solvent in making a flowable is considered novel by the applicant. Still further, the combination of processing steps as described herein helps ensure that a stable and thoroughly mixed formulation is produced.

The first step of the present process is to heat a mixture of at least one solid active fungicidal compound, at least one surfactant and at least one hydrocarbon solvent sufficiently as to form a melt of this mixture. In other words, the heating is carried on for sufficient time and at sufficient temperatures to melt or dissolve the solid fungicidal material in the solvent and surfactant. However, the time and temperatures employed in this step should preferably not be too great so as to decompose or inactive the fungicidal compound or surfactant or to evaporate a major portion of the solvent (i.e., more than 50% by weight of the solvent). Of course, the optimum heating temperatures and times will vary with the particular fungicidal compound, surfactant and solvent employed. Heating temperatures in the range from about 50° C. to about 110° C., and preferably about 90° C. to about 105° C., and heating times from about 1 to 60 minutes, preferably about 15-45 minutes, are generally suitable.

The present invention contemplates that any active solid fungicidal compound may be dissolved during this melting step. Pentachloronitrobenzene, a well known soil and seed fungicide, sold under the trademark TERRACLOR ® by the Olin Corporation, is one especially suitable solid material that may be dissolved by this melting procedure. Normally, pentachloronitrobenzene has a relatively large crystalline structure at room temperature and, in the past, required the use of a grinding procedure in order to use it as a flowable.

Other examples of solid fungicides which may be made into flowable by the present process include cis-N-((trichloromethyl)thio)-4-cyclohexane-1,2-dicarboximide (sold under the common name captan); the sulfate or acetate salt of 9-aza-1,17-diquanidinoheptadecane (sold under the common name guazatine); and 1-hydroxy-2-pyridinethione and its zinc salt (sold by Olin Corporation under the trademark Omadine ® and zinc Omadine ®, respectively). Of course, mixtures of different solid fungicide compounds may be employed.

Besides utilizing just solid fungicide products, it may be desirable to utilize mixtures of both solid and liquid fungicide compounds. For example, it is one preferred embodiment of the present invention to utilize mixtures of the forementioned solid pentachloronitrobenzene and the liquid fungicide, 5-ethoxy-3-(trichloromethyl)-1,2,4-thiadiazole (sold under the trademark TERRAZOLE ® by the Olin Corporation). While this latter compound is usually liquid in nature at room temperatures and, thus, does not require grinding to be made into a flowable; it does react with water to a slight degree and, therefore, will lose some of its fungicidal activity if put directly into an aqueous solution. Accordingly, by first encapsulating this liquid fungicide in a hydrocarbon solvent before adding water as is done by the present invention, it is protected from hydrolysis.

The amount of each fungicide desired in the final formulation will determine to a large degree the relative concentrations of the other ingredients present in the formulation. Once the amount of such active ingredient has been selected, the amounts of each of the other ingredients in the formulation may be determined. The amount of each active fungicide compound for each formulation will vary over a great range depending, of course, on the particular fungicide, or mixtures of fungicides, used; the particular result desired; and a great many other factors. Generally, the total amount of active fungicide compounds in the final formulation will preferably range from about 1% to about 50% by weight of a flowable formulation; more preferably, from about 10% to about 30% by weight.

Any hydrocarbon solvent in which solid fungicide compounds will melt or dissolve and is compatible with the crops and agricultural environment may be employed herein. Suitable examples of such solvents include xylene, kerosene, naphtha and isoparaffinic hydrocarbons. Isoparaffinic hydrocarbons are particularly favored because they are relatively odorless, have a relatively high flash point and are relatively inexpensive as compared to xylene. Accordingly, fungicide distributors and farmers would favor this solvent over xylene because of its better handling properties and ease of application.

One particularly suitable example of isoparaffinic solvents is an essentially odorless, relatively high-boiling, narrow cut isoparaffinic solvent having a typical flash point of 77° C. (170° F.) sold under the trademark Isopar ® M by the Exxon Corporation of Houston, Texas. Isopar ® M is a preferred solvent because it is odorless and has a flash point above about 100° F.

The amount of solvent in the formulation is not critical to the present invention. The optimum amount will depend upon many factors including the amount of active fungicidal compounds present. Generally, it is preferable that the amount of solvent be sufficient for the solid fungicide compounds to melt or dissolve Normally, the amount of solvent is the flowable fungicide formulation will range from about 15% to about 40%, more preferably from about 25% to about 38%, by weight.

Besides the hydrocarbon solvent, it is necessary to add at least one surfactant to the melt-forming mixture. A surfactant must be added before addition of the water is in step (b), discussed below, in order that a stable water-in-oil emulsion be formed. The present invention encompasses the use of any surfactant that is compatible with the active fungicidal compounds and solvent employed and will form a stable water-in-oil emulsion. Organophosphate ester surfactants have been found to be particularly suitable when using an isoparaffinic hydrocarbon solvent like Isopar ® M. Specifically, one organophosphate ester surfactant that is preferred for the present invention is a high viscosity (i.e., about 30,000 centistokes@25° C.) monoester sold under the trademark ATPHOS TM 3220 by ICI Americas, Inc., of Wilmington, Delaware. Moreover, ATPHOS TM 3220 has a high flash point (over 200° F.) and is compatible with nitrogen-containing fertilizers, and antifreezes such as propylene glycol and metals such as molybdenum which may be added to flowables.

The amount of surfactant in the formulation is not critical to the invention and the optimum amount to be employed would vary according to the particular surfactant and other ingredients employed and the particular result desired. Generally, the amount of the surfactant may range from about 2% to about 10%, more preferably, from about 4% to about 8%, by weight.

The surfactant may be added anytime during the heating step including right up to the end of that step. Because its presence is necessary to form a stable water-in-oil emulsion, it should be added before the water-addition step.

The best operating procedure for carrying out this heating step and apparatus employed therein are also not matters of criticality to the present invention and are believed to be within the skill of ordinary artisans. Preferably, it is desirable to add the solid fungicidal compound and the surfactant into the solvent while slowly increasing the heating to the desired melting temperature. Preferably this heating is accomplished by gentle agitation to keep the heat transfer even throughout the solution. It may be preferred to employ a nitrogen gas blanket over the solution to prevent any fires. The construction of the heating apparatus may be any conventional chemical reactor or tank which has heating coils attached or is jacketed. The melting temperature employed will vary with each combination of fungicidal material and solvent used; however, it usually is preferred to keep the melting temperatures in most cases in the range of from about 70° C. to about 100° C., more preferably from about 80° C. to about 90° C. Melting temperatures in excess of the boiling point of water may be undesirable because the excess amounts of the water added in step (b) may turn to steam immediately upon addition.

After the melting is substantially complete, a sufficient amount of an aqueous solution is added to the melt to form a water-in-oil emulsion. The amount of aqueous solution added is not a primary critical parameter of the present invention, but the amount of water added should usually be in the range from about 10 to about 50% of the final flowable formulation, preferably, from about 25% by weight to about 35% by weight to form a flowable.

Besides water, the added aqueous solution may contain other substances. For instance, it is preferred to add a minor portion of propylene glycol and its like with water for antifreeze and emulsion-improving properties. Normally, the amount of propylene glycol, when added, will range from about 1.0% to 10% by weight of the final formulation.

It may be also desirable to add aqueous solutions of metals or fertilizers into the formulation. For example, it may be desirable to add sodium molybdate with the water as a source of the trace mineral molybdenum for the soil. Also, it may be desirable to add an aqueous solution of a nitrogeneous material like urea, ammonium nitrate and the like. The preferred amounts of each of these additional substances besides water must be determined for each particular use. Normally, the melt is added to the tank before the aqueous solution in order to protect the entrapped fungicidal compounds in the melt from being easily hydrolyzed by the water. The ratio of solvent-to-water in most situations will range from about 2:1 to about 0.5:1, more preferably about 1.25:1 to about 0.75:1, by weight.

After the water-in-oil emulsion is formed, it is thoroughly mixed to be substantially homogenized. This mixing step is preferably accomplished by mixing the emulsion in a high shear dispersator or other equivalent mixing equipment. A preferred high shear dispersator is the Premier Series 8000 Dispersator manufactured by the Premier Mill Corporation of New York, N.Y. The time of mixing will depend upon the particular formulation being mixed, the mixer and the specific RPM's employed. Generally, the length of mixing on the Premier Series 8000 Dispersator for most flowable formulations will be from about 1 minute to about 20 minutes at about 7000–8000 RPMs.

It has been found that it is necessary to add a thickening agent to the emulsion during this mixing step in order to form a stable flowable. If a sufficient amount of thickening agent is not added, then the flowable will break apart into different phases during storage. The present invention contemplates that any thickening agent conventionally used in this type of agricultural field may be employed herein. Of course, the optimum thickening agent and its optimum amount in the formulation will depend upon many factors including compatibility with other ingredients in the flowable. A preferred group of thickening agents that have been found to be useful for the present invention are those clays made up mainly of silica. Particularly one commercial silica product found to be useful is sold under the trademark Aerosil ® COK 84 by Degussa Inc. of Tetraboro, New Jersey. This product contains from about 82%–86% silica ($SiO_2$) and about 14%–18% aluminum oxide ($Al_2O_3$). Generally, this product is employed in amounts ranging from about 0.25% to about 3.0% by weight of the final formulation, more preferably from about 0.4% to about 2.0% by weight. Note that such amounts are far less than utilized in conventional flowables.

It is also preferred to add a dye (e.g., purple) during the mixing step to import an unnatural color to the flowable. As state above, the reason for adding the dye is because government regulation requires any agricultural seeds treated with a fungicide to be dyed an unnatural color. In this process, any water- or oil-soluble dye of any unnatural color (e.g., red or violet) may be employed. Normally, the amount of dye added may range from about 0.1% to about 2% of the final formulation.

After mixing, the stable flowable may be packaged or immediately mixed with seed or added to soil. The above formulation may be diluted further by the farmer by addition and mixing in of more water. Of course, the formulation can be employed as made without dilution.

While this invention is discussed only in terms of making flowable fungicidal formulations, it may equally be applicable for making other pesticidal applications including herbicides, insecticides and the like.

The following examples are presented to define the invention more fully without limiting the scope of the invention. All parts and percentages are by weight unless otherwise specified.

EXAMPLES

As shown below in the various Tables, several flowable formulations were prepared according to the process of the present invention. First, combinations of solid and liquid fungicides were added to the surfactant ATPHOS ™ 3220 and the isoparaffinic hydrocarbon solvent Isopar ® M. The various mixtures were then heated to 200° F. in a glass stirred tank in order for the solid fungicides to melt. After melting was completed, an aqueous solution containing water and propylene glycol was then added and mixed in a Premier Series 8000 high shear dispersator for 3–5 minutes. Towards the end of such mixing, a thickening agent Aerosil ® COK 84 was added to the mixer. A violet dye was also added. In some examples, fertilizers such as sodium molybdate and urea-containing fertilizers were also added. The particular formulations that were made up are set forth in the following Tables:

TABLE I

| TERRACLOR ® - 20% TERRAZOLE ® - 5% ||
|---|---|
| Material | % W/W |
| Terraclor ®[1] | 20.2% |
| Terrazole ®[2] | 5.2 |
| Isopar ® M[3] | 34.6 |
| Atphos ™ 3220[4] | 5.0 |
| Water | 30.0 |
| Rhodamine B[5] | 1.0 |

TABLE I-continued

| TERRACLOR® - 20% TERRAZOLE® - 5% | |
|---|---|
| Material | % W/W |
| Aerosil® COK 84[6] | 1.0 |
| Propylene Glycol | 3.0 |
| | 100.0% |

[1] pentachloronitrobenzene sold by the Olin Corporation of Little Rock, Arkansas
[2] 5-ethoxy-3-(trichloromethyl)-1,2,4-thiadiazole sold by the Olin Corporation
[3] odorless, relatively high-boiling, narrow cut isoparaffinic solvent sold by Exxon Corporation of Houston, Texas
[4] high viscosity mono-organophosphate ester surfactant sold by ICI Americas, Inc. of Wilmington, Delaware
[5] Basic Violet 10 dye sold by E. I. duPont de Nemours, Inc. of Wilmington, Delaware
[6] silica clay containing a 5:1 weight ratio of $SiO_2$ to $Al_2O_3$ made by Degussa Inc. of Tetraboro, New Jersey

TABLE II

| TERRACLOR® - 20% TERRAZOLE® - 5% | |
|---|---|
| Material | % W/W |
| Terraclor® | 20.2% |
| Terrazole® | 5.2 |
| Isopar® M | 17.6 |
| Atphos™ 3220 | 5.0 |
| UAN 32 Solution[7] | 50.0 |
| Rhodamine B Dye | 1.0 |
| Aerosil® COK 84 | 1.0 |
| | 100.0% |

[7] an aqueous solution of urea and ammonium nitrate composed of 32% N, 44.3% ammonium nitrate, 35.4% urea and 20.3% water by weight

TABLE III

| TERRACLOR® - 20% | |
|---|---|
| Material | % W/W |
| Terraclor® | 20.2% |
| Isopar® M | 37.8 |
| Atphos™ 3220 | 5.0 |
| Water | 32.0 |
| Rhodamine B Dye | 1.0 |
| Aerosil® COK 84 | 1.0 |
| Propylene Glycol | 3.0 |
| | 100.0% |

TABLE IV

| TERRACLOR® - 20% TERRAZOLE® - 10% | |
|---|---|
| Material | % W/W |
| Terraclor® | 20.2% |
| Terrazole® | 10.6 |
| Isopar® M | 29.6 |
| Atphos™ 3220 | 5.0 |
| Water | 30.0 |
| Rhodamine B Dye | 1.0 |
| Aerosil® COK 84 | 1.0 |
| Propylene Glycol | 3.0 |
| | 100.0% |

TABLE V

| TERRACLOR® - 20% TERRAZOLE® - 5% ZINC OMADINE® - 5% | |
|---|---|
| Material | % W/W |
| Terraclor® | 20.2% |
| Terrazole® | 5.3 |
| Zinc Omadine®[8] | 5.3 |
| Isopar® M | 29.2 |
| Atphos™ 3220 | 5.0 |
| Water | 30.0 |
| Rhodamine B Dye | 1.0 |
| Aerosil® COK 84 | 1.0 |
| Propylene Glycol | 3.0 |

TABLE V-continued

| TERRACLOR® - 20% TERRAZOLE® - 5% ZINC OMADINE® - 5% | |
|---|---|
| Material | % W/W |
| | 100.0% |

[8] the zinc salt of 1-hydroxy-2-pyridinethione sold by the Olin Corporation

TABLE VI

| TERRACLOR® - 20% TERRAZOLE® - 10% ZINC OMADINE® - 10% | |
|---|---|
| Material | % W/W |
| Terraclor® | 20.2% |
| Terrazole® | 10.6 |
| Zinc Omadine® | 10.6 |
| Isopar® M | 21.4 |
| Atphos™ 3220 | 5.0 |
| Water | 27.2 |
| Rhodamine B Dye | 1.0 |
| Aerosil® COK 84 | 1.0 |
| Propylene Glycol | 3.0 |
| | 100.0% |

TABLE VII

| TERRACLOR® - 17% PANOCTINE - 17% | |
|---|---|
| Material | % W/W |
| Terraclor® | 17.3% |
| Panoctine (70%)[9] | 24.3 |
| Isopar® M | 31.9 |
| Atphos™ 3220 | 5.0 |
| Rhodamine B Dye | 1.0 |
| Water | 20.0 |
| Aerosil® COK 84 | 0.5 |
| | 100.0% |

[9] an aqueous solution containing 70% by weight of the acetate salt of 9-aza-1,17-diguanidinoheptadecane and sold by KenoGard AB of Sweden

TABLE VIII

| TERRACLOR® - 24% TERRAZOLE® - 5.9% | |
|---|---|
| Material | % W/W |
| Terraclor® | 24.1% |
| Terrazole® | 6.2 |
| Isopar® M | 29.7 |
| Atphos™ 3220 | 5.0 |
| Rhodamine B Dye | 1.0 |
| Water | 27.0 |
| Aerosil® COK 84 | 1.0 |
| Propylene Glycol | 6.0 |
| | 100.0% |

TABLE IX

| TERRACLOR® - 20% TERRAZOLE® - 5% CAPTAN - 7.5% | |
|---|---|
| Material | % W/W |
| Terraclor® | 20.2% |
| Terrazole® | 5.3 |
| captan 80%[10] | 9.4 |
| Isopar® M | 25.6 |
| Atphos™ 3220 | 5.0 |
| Water | 30.0 |
| Rhodamine B Dye | 1.0 |
| Propylene Glycol | 3.0 |
| Aerosil® COK 84 | 0.5 |
| | 100.0% |

[10] a wettable powder containing 80% cis-N-((trichloromethyl)thio)-4-cyclohexene-1,2-dicarboximide and 20% inert clay sold by Stauffer Chemical Co. of Westport, Connecticut

TABLE X

TERRACLOR® - 10% TERRAZOLE® - 2.5% MOLYBDATE - 12%

| Material | % W/W |
| --- | --- |
| Terraclor® | 10.2% |
| Terrazole® | 2.6 |
| Atphos™ 3220 | 5.0 |
| Isopar® M | 36.2 |
| Sodium Molybdate | 12.6 |
| Water | 30.4 |
| Aerosil® COK 84 | 2.0 |
| Rhodamine B Dye | 1.0 |
| | 100.0% |

TABLE XI

TERRACLOR® - 20% TERRAZOLE® - 5%

| Material | % W/W |
| --- | --- |
| Terraclor® | 20.2% |
| Terrazole® | 5.2 |
| Isopar® M | 35.6 |
| Atphos™ 3220 | 5.0 |
| Water | 30.0 |
| Rhodamine B Dye | 0.5 |
| Aerosil® COK 84 | 0.5 |
| Propylene Glycol | 3.0 |
| | 100.0% |

TABLE XII

TERRACLOR® - 20%

| Material | % W/W |
| --- | --- |
| Terraclor® | 20.5% |
| Isopar® M | 40.5 |
| Atphos™ 3220 | 5.0 |
| Water | 30.0 |
| Rhodamine B Dye | 0.5 |
| Aerosil® COK 84 | 0.5 |
| Propylene Glycol | 3.0 |
| | 100.0% |

What is claimed is:

1. A process for producing a flowable fungicide formulation comprising the steps of:
   (a) heating at least one solid active fungicidal compound, a hydrocarbon solvent, and a surfactant to reduce the particle size of said solid fungicidal compound and to form a liquid melt from said mixture;
   (b) adding an aqueous solution to said melt to form a water-in-oil emulsion; and
   (c) thoroughly mixing said emulsion in the presence of an amount of a thickening agent to form a stable flowable fungicide formulation, said flowable fungicide formulation comprising from about 1% to about 50% by weight of active fungicidal compounds, from about 15% to about 40% by weight of said hydrocarbon solvent, from about 2% to about 10% by weight of said surfactant, from about 10% to about 50% by weight of water, and from about 0.25% to about 3% by weight of said thickening agent.

2. The process of claim 1 wherein said solid active fungicidal compound is pentachloronitrobenzene.

3. The process of claim 1 wherein a liquid active fungicidal compound is also added during melting step (a).

4. The process of claim 3 wherein said liquid active fungicidal compound is 5-ethoxy-3-(trichloromethyl)-1,2,4,-thiadiazole.

5. The process of claim 4 wherein said solid liquid active fungicidal compound is pentachloronitrobenzene.

6. The process of claim 1 wherein said heating step is carried out at a temperature in the range from about 50° C. to about 110° C.

7. The process of claim 1 wherein said aqueous solution comprises water and propylene glycol.

8. The process of claim 7 wherein said aqueous solution further comprises nitrogeneous material selected from the group consisting of urea, ammonium nitrate and mixtures thereof.

9. The process of claim 1 wherein the amount of water added is in the range from about 25% to about 35% by weight of said flowable formulation.

10. The process of claim 1 wherein said thickening agent is a silica-containing compound.

11. The product made according to the process of claim 1.

12. The process of claim 1 wherein the amount of said active fungicidal compounds is from about 10% to about 30% by weight of said flowable formulation.

13. The process of claim 1 wherein the amount of said hydrocarbon solvent is from about 25% to about 38% by weight of said flowable formulation.

14. The process of claim 1 wherein the amount of said surfactant is from about 4% to about 8% by weight of said flowable formulation.

15. The process of claim 1 wherein the amount of said thickening agent is from about 0.4% to about 2% of said flowable formulation.

16. The process of claim 1 wherein said flowable formulation comprises from about 10% to about 30% by weight of said active fungicidal compounds, from about 25% to about 38% by weight of said hydrocarbon solvent, from about 4% to about 8% by weight of said surfactant, from about 25% to about 35% by weight water, and from about 0.4% to about 2% by weight of said thickening agent.

17. A process for producing a flowable fungicide formulation comprising the steps of:
   (a) heating a mixture of solid pentachloronitrobenzene, an isoparaffinic hydrocarbon solvent and an organophosphate ester surfactant to reduce the particle size of said solid pentachloronitrobenzene and to form a liquid melt from said mixture;
   (b) adding an aqueous solution comprising water and propylene glycol to said melt so as to form a water-in-oil emulsion; and
   (c) thoroughly mixing said emulsion in a high shear dispersator in the presence of a silica-containing thickening agent to form a stable flowable fungicide formulation, said flowable formulation comprising from about 1% to about 50% of total active fungicide compounds, from about 15% to about 40% by weight of said isoparaffinic hydrocarbon solvent from about 2% to about 10% by weight of said organophosphate ester surfactant, from about 10% to about 50% by weight of said water, from about 1% to about 10% by weight of propylene glycol, and from about 0.25% to about 3% by weight of said silica-containing thickening agent.

18. The process of claim 17 wherein the mixture of step (a) also contain the liquid fungicide, 5-ethoxy-3-(trichloromethyl)-1,2,4-thiadiazole.

19. The process of claim 17 wherein said heating step is carried out a temperature in the range from about 90° C. to about 105° C.

20. The process of claim 17 wherein said aqueous solution further comprises nitrogeneous material selected from the group consisting of urea, ammonium nitrate and mixtures thereof.

21. The process of claim 17 wherein the amount of water added is in the range of about 25% to about 35% by weight of said flowable formulation.

22. The process of claim 17 wherein said silica-containing thickening agent contains about 82-86% silica and about 18-14% aluminum oxide.

23. The product made according to the process of claim 17.

24. The process of claim 17 wherein the amount of active fungicidal compounds is from about 10% to about 30% by weight of said flowable formulation.

25. The process of claim 17 wherein the amount of said isoparaffinic hydrocarbon solvent is from about 25% to about 38% by weight of said flowable formulation.

26. The process of claim 17 wherein the amount of said organophosphate ester surfactant is from about 4% to about 8% by weight of said flowable formulation.

27. The process of claim 17 wherein the amount of said silica-containing thickening agent is from about 0.4% to about 2% by weight of said flowable formulation.

28. The process of claim 17 wherein said flowable formulation comprises from about 10% to about 30% by weight of active fungicidal compounds, from about 25% to about 38% by weight of said isoparaffinic hydrocarbon solvent, from about 4% to about 8% by weight of said organophosphate ester surfactant, from about 25% to about 35% by weight of water, and from about 0.4% to about 2% by weight of said silica-containing thickening agent.

* * * * *